(12) United States Patent
Purga et al.

(10) Patent No.: US 8,408,904 B2
(45) Date of Patent: Apr. 2, 2013

(54) COUPLING FOR A MULTI-PART DENTAL IMPLANT SYSTEM

(75) Inventors: Johnny Purga, Laufen (CH); Ulrich Mundwiler, Tenniken (CH); Andreas Utz, Freiburg (DE)

(73) Assignee: Straumann Holding AG, Basel (CH)

( * ) Notice: Subject to any disclaimer, the term of this patent is extended or adjusted under 35 U.S.C. 154(b) by 0 days.

(21) Appl. No.: 11/921,480

(22) PCT Filed: May 23, 2006

(86) PCT No.: PCT/EP2006/004919
§ 371 (c)(1),
(2), (4) Date: Jan. 8, 2008

(87) PCT Pub. No.: WO2006/128620
PCT Pub. Date: Dec. 7, 2006

(65) Prior Publication Data
US 2009/0123890 A1    May 14, 2009

(30) Foreign Application Priority Data
Jun. 3, 2005   (EP) .................................. 05104832

(51) Int. Cl.
*A61C 8/00* (2006.01)

(52) U.S. Cl. ........................................ 433/173; 433/174

(58) Field of Classification Search .................. 433/172, 433/173, 174, 201.1
See application file for complete search history.

(56) References Cited

U.S. PATENT DOCUMENTS

| | | | |
|---|---|---|---|
| 5,281,140 A | 1/1994 | Niznick | |
| 5,667,384 A | 9/1997 | Sutter et al. | |
| 5,947,733 A | 9/1999 | Sutter et al. | |
| 5,984,680 A * | 11/1999 | Rogers | 433/173 |
| 6,227,859 B1 | 5/2001 | Sutter | |
| 7,249,949 B2 * | 7/2007 | Carter | 433/173 |

FOREIGN PATENT DOCUMENTS

| | | |
|---|---|---|
| EP | 1 396 236 | 3/2004 |
| JP | 11-506688 A | 6/1999 |
| JP | 2003-518980 A | 6/2003 |
| WO | 01/49199 A2 | 7/2001 |

OTHER PUBLICATIONS

Japanese Office Action dated Aug. 16, 2011 issued in Japanese Patent Application No. 2008-513979 together with partial English language translation.

* cited by examiner

*Primary Examiner* — Cris L Rodriguez
*Assistant Examiner* — Eric Rosen
(74) *Attorney, Agent, or Firm* — Scully, Scott, Murphy & Presser, P.C.

(57) ABSTRACT

The invention relates to an abutment for use in a dental implant system, wherein the abutment is provided with a guiding and lock element for associating the abutment to a dental implant, the guiding and lock element including: a first conically tapered section; a second substantially non-tapered section arranged apically adjacent to the first section, the second section being provided with an anti-rotational element; and a third substantially circular cylindrical section arranged apically adjacent to the second section, such that to provide axial guiding to the abutment upon the insertion thereof into a dental implant. Further, the invention relates to a dental implant formed in a similar manner.

8 Claims, 7 Drawing Sheets

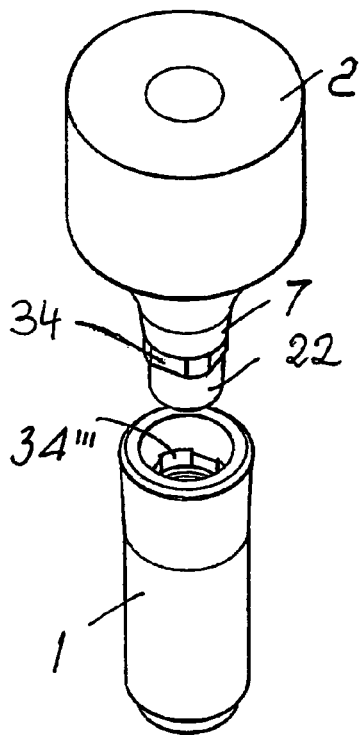
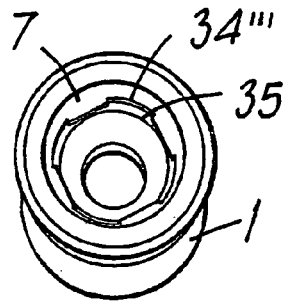
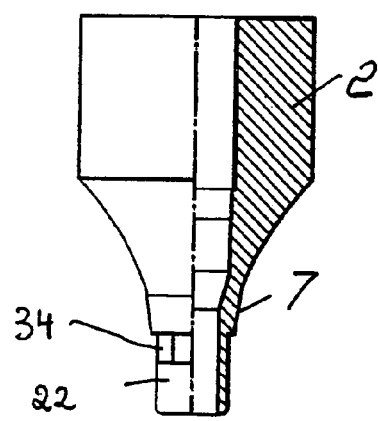
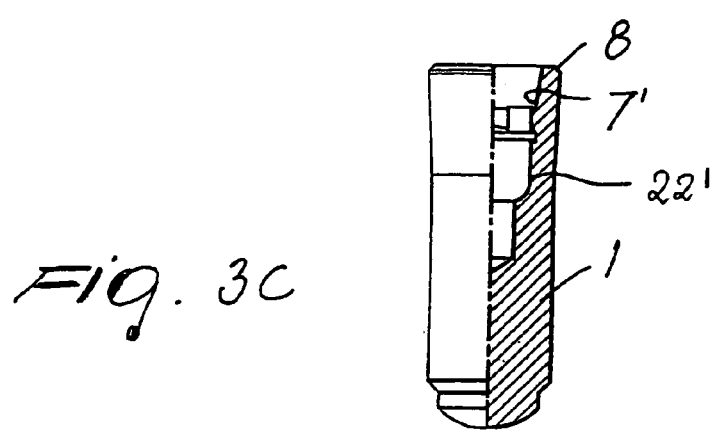
Fig. 3A
Fig. 3B
Fig. 3C

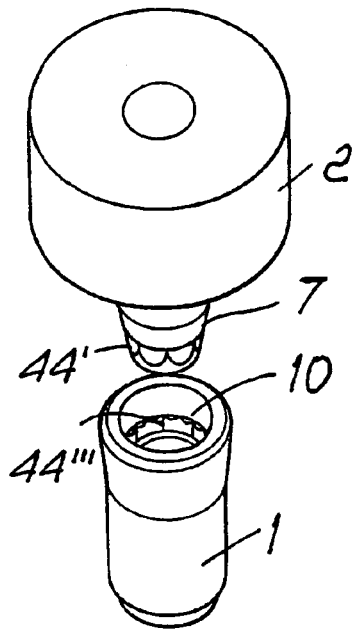
Fig. 4A
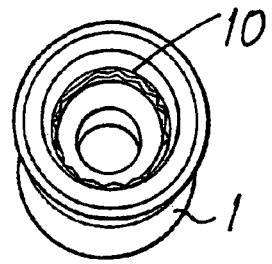
Fig. 4B
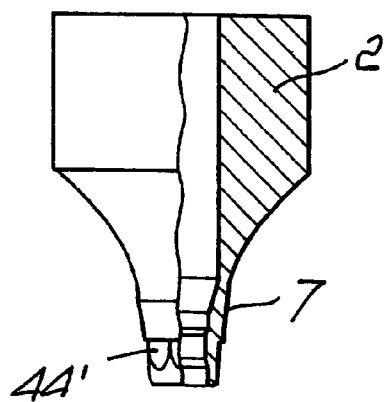
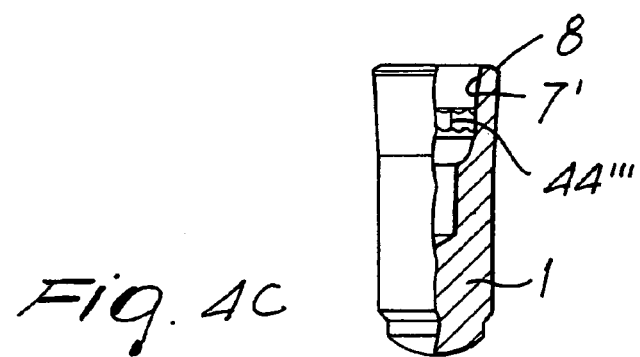
Fig. 4C

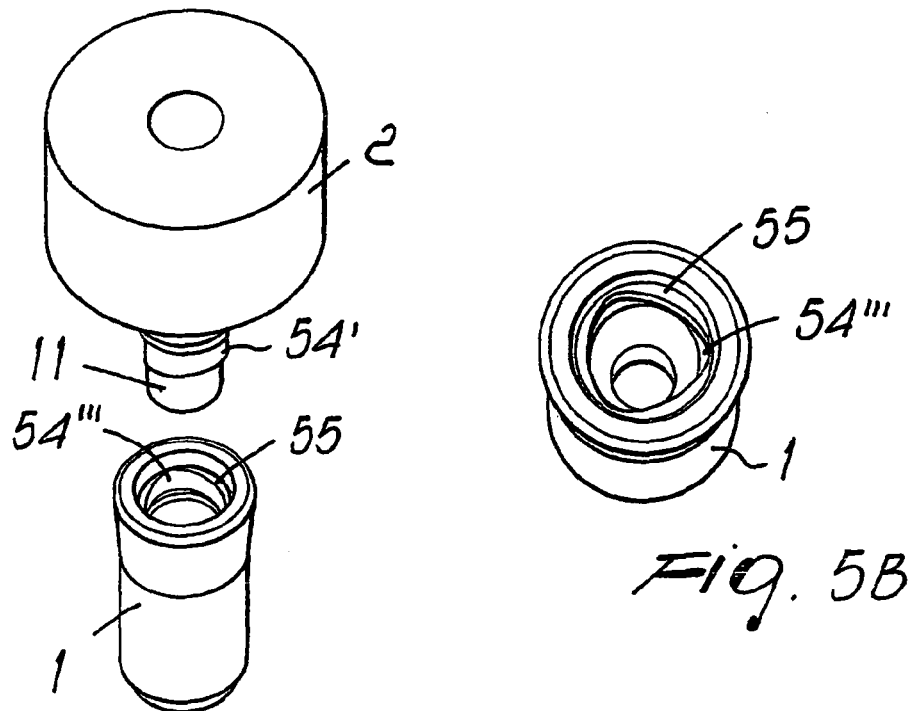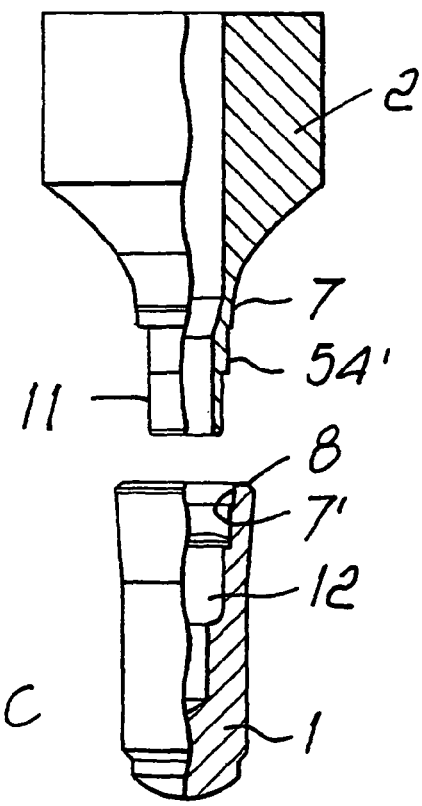

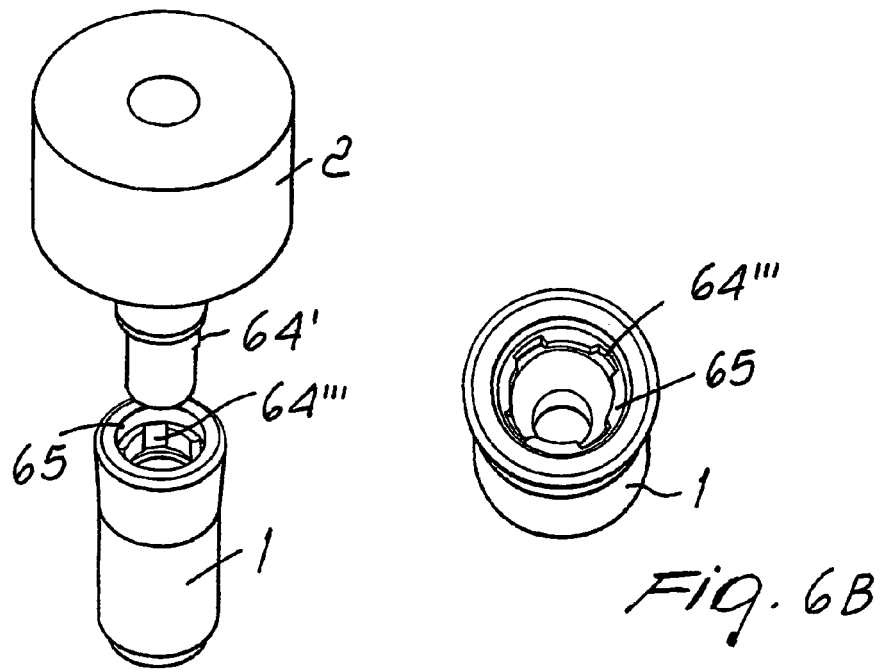
Fig. 6A
Fig. 6B
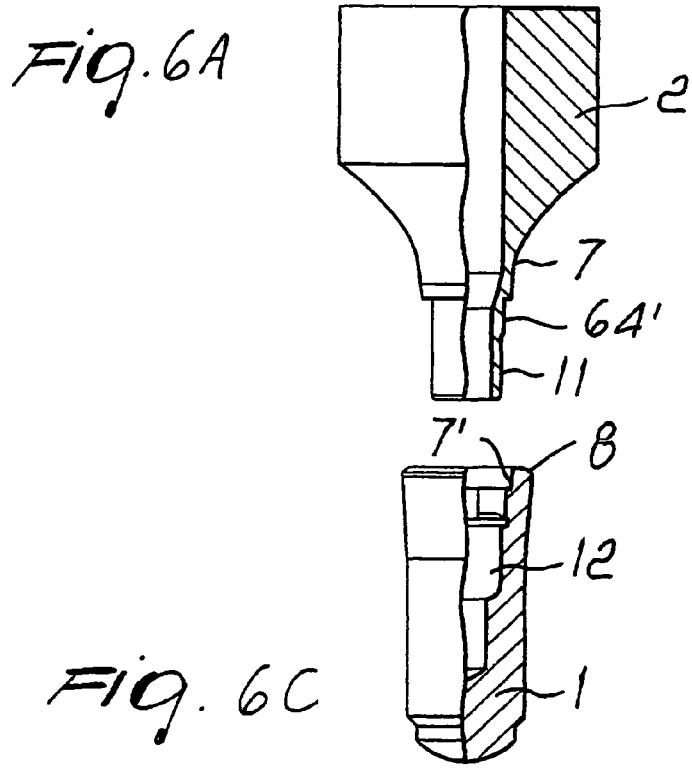
Fig. 6C

COUPLING FOR A MULTI-PART DENTAL IMPLANT SYSTEM

The present invention relates in general to an improved coupling for a multi-part dental implant system and in particular to an improved coupling for a dental implant with an abutment, a secondary part or the like.

BACKGROUND OF THE INVENTION

Generally, multi-part dental implant systems are used in dental surgery to reconstruct dental parts of a human being. Usually, multi-part implant systems are comprised of a dental implant, preferably a dental implant screw, which is inserted by screwing or pressing into a receiving bore which has been prepared e.g. in the bone tissue and abutments or secondary parts adapted, inter alia, to support a dental prosthesis.

A frequent problem arising with the above described multi-part dental implant systems is the correct positioning of the abutment or the secondary part within the dental implant already placed in the bone tissue.

The problem of the correct positioning was addressed by numerous prior art patent publications.

In particular, according to U.S. Pat. No. 5,195,852, a cylindrical cavity was devised, at the coronal end of the dental implant screw, to include a plurality of striations for preventing the rotation of the abutment supporting a prosthetic structure. However, as the striations were provided right at the upper end surface of the dental implant screw, the stability and sterility of the coupling between the abutment and the dental implant screw was unsatisfactory.

Another solution was proposed by U.S. Pat. No. 5,281,140 wherein a three part dental implant system comprised of a dental implant, a first intermediate abutment part and a second distal abutment part was disclosed. The dental implant was provided at the coronal end thereof with a chamfered shoulder, followed by a hexagonal opening extending apically into the dental implant and followed further apically by an internally-threaded cylindrical-shaped passage adapted to receive a fastener screw. The first intermediate abutment part was shaped at the apical end thereof complementary to the chamfered shoulder and the hexagonal opening of the dental implant, respectively, and provided with a multi-sided projection at its side facing the second distal abutment part. Further, the second distal abutment part was shaped at an apical end thereof with a cavity complementary to the multi-sided projection of the first intermediate abutment part, such as to provide for the relative rotational positioning of the two abutments when coupled via the fastener screw to the dental implant.

Nonetheless, the solution of U.S. Pat. No. 5,281,140 was also not free of shortcomings due to the larger number of parts involved. Also the relatively large taper degree of the chamfered shoulder was not suitable to provide for a sufficiently stable and sterile coupling of the abutment parts to the dental implant.

EP-A-475 299 discloses a dental implant screw which is connectable to a two part abutment, wherein the dental implant is provided with centering and positive lock means spaced from its shoulder and wherein a short cylindrical recess extends between the centering means and the shoulder. EP-A-475 299, however, also fails to provide for a sufficiently stable and sterile coupling of the abutment parts to the dental implant screw.

SUMMARY OF THE INVENTION

The aim of the present invention is to provide an improved coupling for a multi-part dental implant system and in particular an improved coupling for a dental implant with an abutment, a secondary part or the like which avoids the drawbacks of the prior art devices, and thus allows a stable and sterile coupling between the dental implant and the abutment and the secondary part, respectively.

Within the scope of this aim, an object of the present invention is to provide an improved coupling for a multi-part dental implant system, wherein the positioning of the abutment or the secondary part can be accurately performed even by a user who is less experienced. In fact, it will be appreciated by the person skilled in the art that the positioning of the abutment or of the secondary part on the dental implant is not a trivial matter having regards of the small dimensions of the parts involved and the working environment. At any rate, the solution proposed by the present invention to the above object is intended not to be detrimental to sterility and stability of the coupling.

Another object is to provide an improved coupling for a multi-part dental implant system, wherein the number of parts is minimized.

This aim, these objects and other which will become better apparent hereinafter, are achieved by a coupling for a multi-part dental implant system as defined in the appended claims.

In particular, the present invention provides in certain embodiments thereof for an abutment for use in a dental implant system, wherein the abutment is provided with guiding and lock means for associating the abutment to a dental implant, the guiding and lock means including: a first conically tapered section; a second substantially non-tapered section arranged apically adjacent to the first section, the second section being provided with anti-rotational means; and a third substantially circular cylindrical section arranged apically adjacent to the second section, such that to provide axial guiding to the abutment upon the insertion thereof into a dental implant. In an analogous manner, an complementary matter to above, the invention provides for a dental implant for use in a dental implant system, wherein the dental implant is provided with a guiding and lock means for associating the dental implant to an abutment, the guiding and lock means including: a first conically tapered section; a second substantially non-tapered section arranged apically adjacent to the first section, the second section being provided with an anti-rotational means; and a third substantially circular cylindrical section arranged apically adjacent to the second section, such that to provide axial guiding to an abutment upon the insertion thereof into the dental implant In other embodiments of the invention an abutment for use in a dental implant system is disclosed, wherein the abutment is provided with a guiding and lock means for associating the abutment to a dental implant, the guiding and lock means including: a first conically tapered section; and a second substantially non-tapered section arranged apically adjacent to the first section, the second section being provided with an anti-rotational means, wherein the anti-rotational means of the second section includes a surface extending radially with respect to the axis of the abutment and adapted to cooperate with a dental implant, such that to provide radial guiding to the abutment upon the insertion into the implant. In a similar manner the invention also teaches a dental implant for use in a dental implant system, wherein the dental implant is provided with a guiding and lock means for associating the dental implant to an abutment, the guiding and lock means including: a first conically tapered section; and a second substantially non-tapered section arranged apically adjacent to the first section, the second section being provided with an anti-rotational means, wherein the anti-rotational means of the second section includes a surface extending radially with respect to the axis of the dental implant and adapted to cooperate with an abutment, such that to provide radial guiding to the abutment upon the insertion into the implant.

BRIEF DESCRIPTION OF THE DRAWINGS

Further characteristics and advantages of the present invention will become better apparent from the following description of a preferred but not exclusive embodiment of the implant system according to the invention, illustrated by way of non-limitative example in the accompanying drawings, wherein:

FIG. 3A is a perspective view of a coupling for a multi-part dental implant system according to a third embodiment of the invention;

FIG. 3B is an upper view of a dental implant provided with the coupling according to the third embodiment of the invention;

FIG. 3C is a side view of the guiding and lock means of the dental implant and the corresponding guiding and lock means of an abutment or a secondary part according to the third embodiment of the invention;

FIG. 4A is a perspective view of a coupling for a multi-part dental implant system according to a fourth embodiment of the invention;

FIG. 4B is an upper view of a dental implant provided with the coupling according to the fourth embodiment of the invention;

FIG. 4C is a side view of the guiding and lock means of the dental implant and the corresponding guiding and lock means of an abutment or a secondary part according to the fourth embodiment of the invention;

FIG. 5A is a perspective view of a coupling for a multi-part dental implant system according to a fifth embodiment of the invention;

FIG. 5B is an upper view of a dental implant provided with the coupling according to the fifth embodiment of the invention;

FIG. 5C is a side view of the guiding and lock means of the dental implant and the corresponding guiding and lock means of an abutment or a secondary part according to the fifth embodiment of the invention;

FIG. 6A is a perspective view of a coupling for a multi-part dental implant system according to a sixth embodiment of the invention;

FIG. 6B is an upper view of a dental implant provided with the coupling according to the sixth embodiment of the invention; and FIG. 6C is a side view of the guiding and lock means of the dental implant and the corresponding guiding and lock means of an abutment or a secondary part according to the sixth embodiment of the invention.

DETAILED DESCRIPTION OF THE INVENTION

Figure 1A:
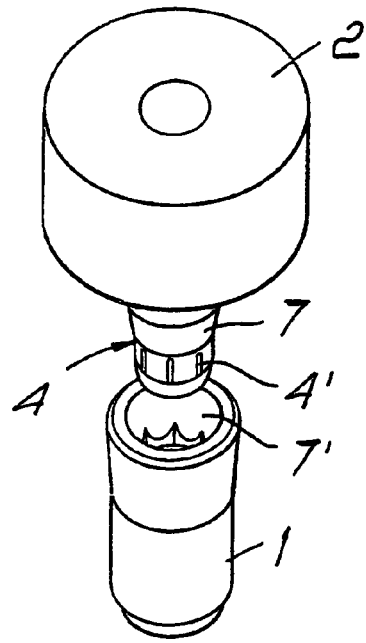
FIG. 1A is a perspective view of a coupling for a multi-part dental implant system according to a first embodiment of the invention.
Figure 1B:
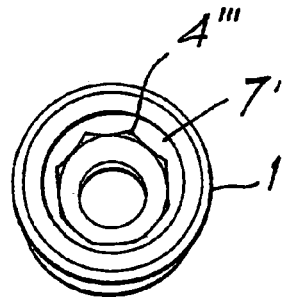
FIG. 1B is an upper view of a dental implant provided with the coupling according to the first embodiment of the invention.
Figure 1C:
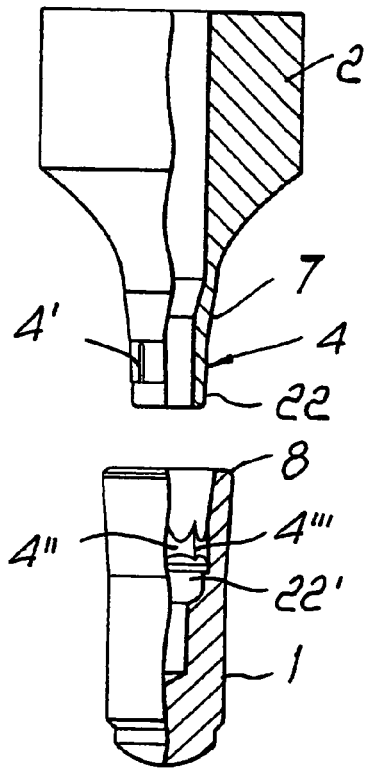
FIG. 1C is a side view of the guiding and lock means of the dental implant and the corresponding guiding and lock means of the abutment or the secondary part according to the first embodiment of the invention.
Figure 1D:
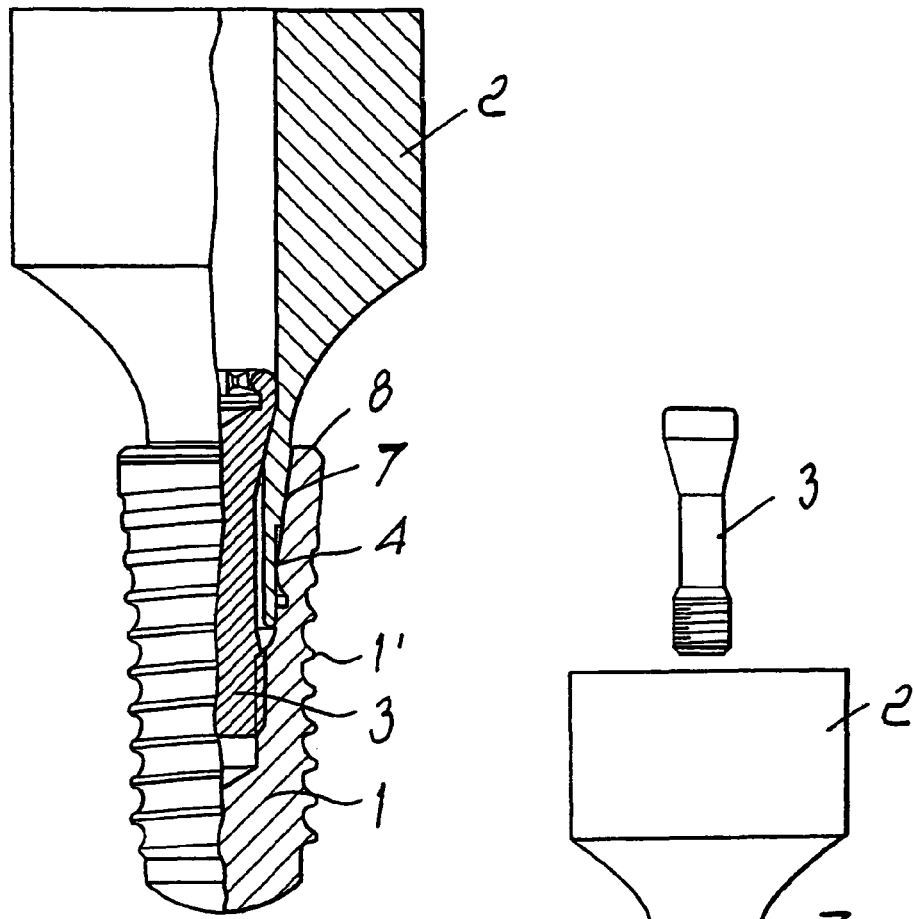
FIG. 1D is a view of a dental implant assembled with the abutment and including the coupling according to the first embodiment of the present invention.
Figure 1E:
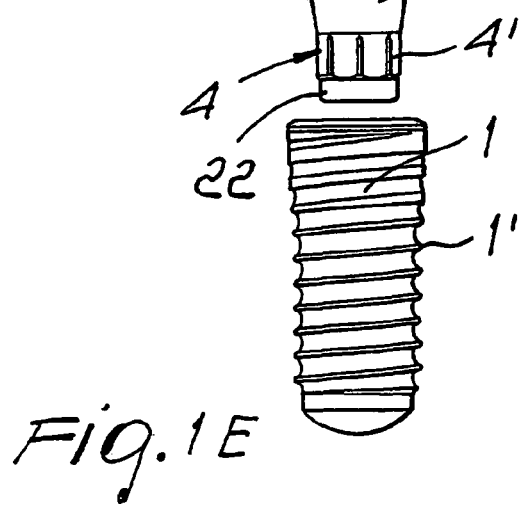
FIG. 1E is an overall view of the dental implant system incorporating the coupling according to the first embodiment of the present invention.

With reference to the enclosed FIGS. 1A through 1E there is shown a dental implant 1, preferably a dental implant having an external thread for insertion into a bone tissue, an abutment or secondary part 2 and a threaded fastener screw 3 forming together a dental implant system. The threaded fastener screw 3 is preferably axially hold in the abutment, as best seen in FIG. 1D.

According to the first embodiment of the present invention, the abutment 2 is provided with guiding and lock means implemented as a first conically tapered section 7, followed, in a further apical position, by a second substantially non-tapered section 4 with protrusions 4' extending in an axial direction of the abutment 2 and followed, in further remote apical position, by a third substantially circular cylindrical section 22.

The number of protrusions shown in FIGS. 1A through 1E is equal to eight. This results in a substantially octagonal cross-section of the second non-tapered section 4. Nevertheless, the person skilled in the art will appreciate that the number of protrusions may be varied as need be to adjust the number of relative positions between the dental implant 1 and the abutment 2. Also the shape of the protrusions 4' may be varied, such that the resulting cross-section of the respective abutment section is not necessarily octagonal.

According to the present first embodiment, it has been found that it is particularly advantageous if the axial extension of second section 4 is about twice the axial extension of the third section 22. Further, it has been found that it is particularly advantageous if the axial extension of the first section 7 is approximately equal to the overall axial extension of the second 4 and third 22 sections taken together. Therefore, the user is provided with a longer insertion path and consequently with a better feedback when assembling the abutment to the dental implant. In addition, the fastening (or threading) of the screw 3 to a dental implant is only possible once the second section 4 along with the third section 22 are fully inserted into their complementary sections of the dental implant, as will be described hereinafter. In this way a wedging of the screw can be avoided.

According to the present invention, it has also been found that the taper of the first section 7 with respect to the axis of the abutment 2 is in the order of about 6° to about 10°, preferably about 7° to about 9° and most preferably about 8° such that sealing and stability requirements of the coupling between the dental implant and the abutment are met. In addition, it has been found that the axial extension of the first section 7 is preferably, as explained, in the order of about the overall axial length of the second 4 and third 22 sections taken together. The latter also further improves the sealing and stability characteristic of the dental implant system of the present invention.

The dental implant 1 is provided with guiding and lock means that are complementary to the guiding and lock means of the abutment 2, namely a first conically tapered section 7' matching the first conically tapered section 7 of the abutment 2, a second substantially non-tapered section 4" with grooves 4''' adapted for receiving the second substantially non-tapered section 4 and the protrusions 4' of the abutment 2, and a third substantially circular cylindrical section 22' adapted for receiving the third section 22 of the abutment. As the first 7', second 4", and third 22' sections of the dental implant 1 are, as set forth above, complementary to the first 7, second 4, and third 22 sections of the abutment 2 as regards shape, extension, taper angle etc., the detailed description thereof will be omitted for the sake of avoiding repetitions. Nonetheless, the person skilled in the art will appreciate that the number of protrusions must not equate the number of grooves, as also apparent from some of the embodiments described hereinbelow.

According to the present invention the shoulder 8 of the dental implant 1 is free of grooves and the grooves/protrusions providing for the anti-rotation lock between the dental implant 1 and the abutment 2 are displaced from the shoulder 8. Therefore, the sealing characteristics of the dental implant system at the interface between the dental implant and the abutment are not impaired and the sterility thereof is maintained. In addition, the jamming of the protrusions 4' is avoided upon the insertion of the abutment 2 into the dental implant 1 due to presence of the first tapered sections 7 and 7'.

Moreover, by means of the taper fitting, an efficient anti-bacterial barrier is created as no micro gap is present between the dental implant 1 and the abutment 2 and the exact matching of the latter parts hinders relative micro displacements therebetween. Further, by tightening the fastener screw 3, a double anti-rotation lock is achieved, namely a positive lock by means of the protrusion/groove interaction and a frictional lock by means of the interaction between two tapered sections 7 and 7'.

Furthermore, the third sections 22 and 22' of the abutment 2 and dental implant 1, respectively, provide for a guiding function that facilitates the insertion of the abutment 2 into the dental implant 1.

It should be noted that the advantages listed above apply to all of the embodiments described herein, although the guiding function may be achieved in a different manner to be described hereinbelow.

Figure 2A:
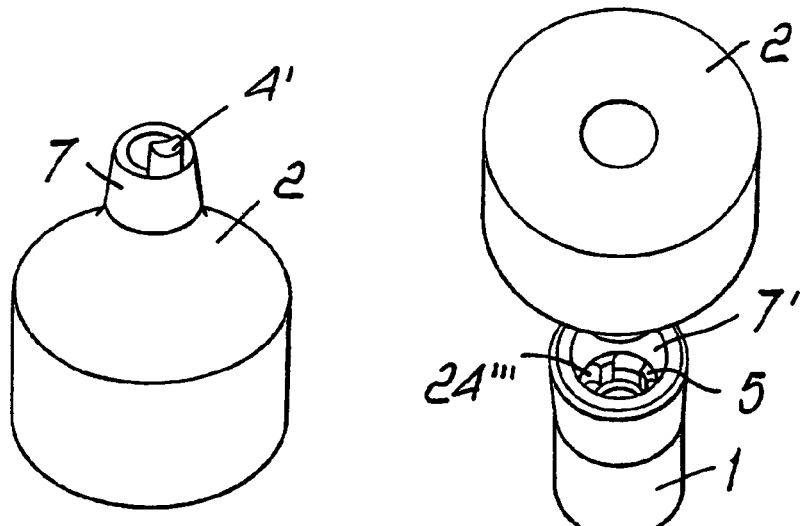
FIG. 2A is a perspective view of a coupling for a multi-part dental implant system according to a second embodiment of the invention.
Figure 2B:
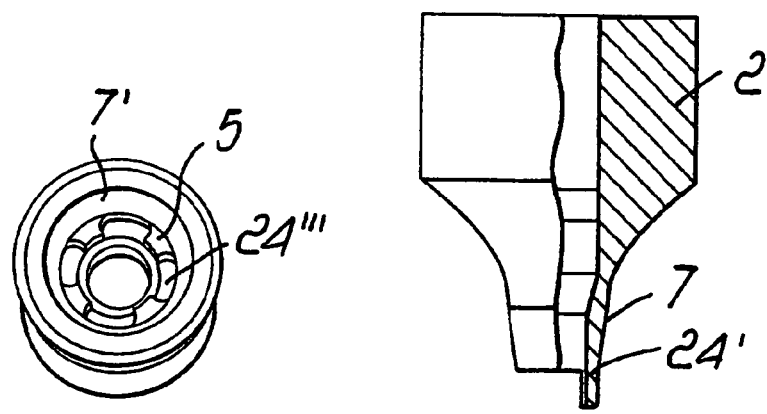
FIG. 2B is an upper view of a dental implant provided with the coupling according to the second embodiment of the invention.
Figure 2C:
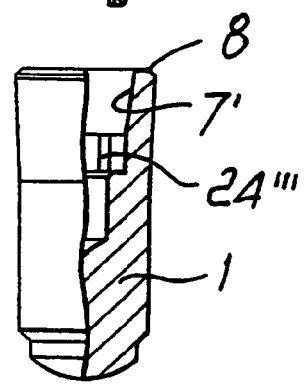
FIG. 2C is a side view of the guiding and lock means of the dental implant and the corresponding guiding and lock means of an abutment or a secondary part according to the second embodiment of the invention.

A second embodiment of the present invention is described with regard to FIGS. 2A through 2C wherein features similar to those of the first embodiment of the invention are designated by the same reference numerals, and therefore the description thereof will be omitted to the extent of the overlap with the first embodiment of the invention.

In the second embodiment, the second and the third sections of the abutment 2 are replaced by a protrusion 24' that is provided apically adjacent to the first section 7 thereof. For the sake of better understanding the abutment is also shown in an inverted view in FIG. 2A.

In the dental implant 1 of the second embodiment the second and third sections are, in turn, replaced by an annular platform 5 with grooves 24''' which provide for a rosetted appearance to the guiding and lock means of the dental implant 1. While four grooves 24''' are shown in FIGS. 2A and 2B, the person skilled in the art will readily understand that their number can be varied as need be, for instance to adjust the number of relative positions between dental implant and abutment.

The improved handling of the second embodiment of the invention is achieved by placing the abutment 2 with its protrusion 24' on the annular platform 5 of the dental implant 1 in an intermediate position. In this position it is not possible to tighten the fastener screw 3. Therefore, an improved jamming safety is provided to the abutment. Tightening of the fastener screw 3 is only possible if the protrusion 24' is rotated until it is brought in registration with one of the grooves 24''' and fully penetrates it. In this way, the second embodiment of the invention provides for an advantageous implementation of the guiding function that facilitates the insertion of the abutment 2 into the dental implant 1.

A third embodiment of the present invention is described with regard to FIGS. 3A through 3C wherein features similar to those of the first embodiment of the invention are designated by the same reference numerals, and therefore the description thereof will be omitted to the extent of the overlap with the first embodiment of the invention.

In the abutment of the third embodiment of the invention, the second section 34 is implemented with a substantially octagonal cross-section, with four straight sides connected by four interposed protruding sides, each of the protruding sides having preferably a curved shape. In fact, expressed in an exaggerated manner, the cross-section resembles to a square with rounded edges. The substantially cylindrical third section 22 of the abutment 2 is similar to the third section 22 of the abutment of the first embodiment.

In the third embodiment of the invention, the second section of the dental implant 1 is replaced yet again by a platform 35 with four grooves 34''' which provide for the above described square appearance with rounded edges to the guiding and lock means of the dental implant 1. In other words, the outline or the cross-section of the platform 35 and the grooves 34''' of the dental implant is complementary to the outline or cross-section of the second section 34 of the abutment 2. The third section 22' of the dental implant is complementary to the third section 22 of the abutment 2.

The improved handling of the third embodiment of the present invention is achieved by placing the abutment 2 with its second section 34 (forming the square outline with rounded edges) on the platform 35 of the dental implant 1 in an intermediate position, such that the straight sides of the second section 34 of the abutment 2 rest on the platform 35 of the dental implant. In this position it is not possible to tighten the fastener screw 3. Therefore, an improved jamming safety is provided to the abutment. Tightening of the fastener screw 3 is only possible if the second section 34 of the abutment 2 is rotated into registration with the grooves 34'''. In this way, the third embodiment of the present invention provides for an advantageous implementation of the guiding function that facilitates the insertion of the abutment 2 into the dental implant 1. Furthermore, the guiding function is enhanced by the presence of the respective third sections on the abutment and dental implant.

A fourth embodiment of the present invention is described with regard to FIGS. 4A through 4C wherein features similar to those of the third embodiment of the invention are designated by the same reference numerals, and therefore the description thereof will be omitted to the extent of the overlap with the third embodiment of the invention.

In the fourth embodiment of the invention the abutment 2 is provided with eight protrusion 44' (forming a substantially octagonal outline) while the dental implant 1 is provided with eight matching grooves 44''' (also forming a substantially octagonal outline) and adapted to receive the protrusions 44'. Again, it is stressed that the number of protrusions and of the matching grooves can be varied as need be.

Advantageously, in the fourth inventive embodiment, there is provided around the grooves 44''' a SCS-ring 10 which functions as a force transmission element. Thus, the grooves 44''' of the dental implant 1 serve only as (rotational) positioning or re-positioning elements and are not subjected to stress due to force transmission.

A fifth embodiment of the present invention is described with regard to FIGS. 5A through 5C wherein features similar to those of the first embodiment of the invention are designated by the same reference numerals, and therefore the description thereof will be omitted to the extent of the overlap with the first embodiment of the invention.

In the fifth embodiment of the invention the abutment 2 is provided with three protrusions 54' (forming a substantially triangular outline) while the dental implant 1 is provided with three matching grooves 54''' (also forming a substantially triangular outline) and adapted to receive the protrusions 54'. Such substantially triangular outline allows a better force transmission.

Moreover, in a similar manner to the second inventive embodiment, there is provided an annular platform 55 surrounding the grooves 54'''. Accordingly, in a similar manner to the second embodiment an improved jamming safety is provided to the abutment 2, as the abutment 2 is held in an intermediate position on the annular platform 55 until the protrusions 54' are rotated into registration with the grooves 54''' such that the abutment 2 fully penetrates the dental implant 1 and may be firmly fastened by the fastener screw 3 thereto.

A particular feature of the fifth embodiment is the extended cylindrical third section designated by reference numeral 11 provided at the apical end of the abutment 2 adjacent to the second non-tapered section, the extended cylindrical third section 11 providing, in conjunction with a matching third section 12 in the dental implant 1, for a better support and guiding of the abutment 2. Preferably, the axial extension of the extended third section 11 of the abutment is such that the ratio thereof to the axial extension of the second section of the abutment 2 is from about 1.4 to 1.7 and more preferably 1.6. As can be seen with particular reference to FIG. 5C the axial extension of the first section of the abutment is about one half of the axial extension second section thereof.

A sixth embodiment of the present invention is described with regard to FIGS. 6A through 6C wherein features similar to those of the first embodiment of the invention are designated by the same reference numerals, and therefore the description thereof will be omitted to the extent of the overlap with the first embodiment of the invention.

In the sixth embodiment of the invention the abutment 2 is provided with one single protrusion 64' while the dental implant 1 is provided with a plurality (e.g. four) matching grooves 64'' and adapted to receive the protrusion 64'.

Further, in a similar manner to the second or fifth inventive embodiment, there is provided an annular platform 65 interposed between the grooves 64'''. Thus, an improved jamming safety is provided to the abutment 2, as the abutment 2 is held in an intermediate position on the annular platform 65 until the protrusion 64' is rotated into registration with one of the grooves 64''' such that the abutment 2 fully penetrates the dental implant 1. Also, the guiding and support function in the sixth embodiment is enhanced by the presence of the respective extended third sections on the abutment and dental implant, wherein the sections are devised to have an axial extension similar to that of the fifth embodiment.

Clearly, several modifications will be apparent to and can be readily made by the person skilled in the art without departing from the scope of the present invention. Therefore, the scope of the claims shall not be limited by the illustrations or the preferred embodiments given in the description in the form of examples, but rather the claims shall encompass all of the features of patentable novelty that reside in the present invention, including all the features that would be treated as equivalents by the person skilled in the art. In this regard it is stressed that the dental implant and abutment of the invention can be manufactured from ceramics, metal (in particular titan) and combinations thereof.

Where technical features mentioned in any claim are followed by reference signs, those reference signs have been included just for the sole purpose of increasing intelligibility of the claims and accordingly, such reference signs do not have any limiting effect on the scope of each element identified by way of example by such reference signs.

What is claimed is:

1. A dental implant system comprising a dental implant, an abutment and a threaded screw, the abutment being provided with a guiding and lock means for associating the abutment to the dental implant, the guiding and lock means comprising:
   a first conically tapered section; and
   a second non-tapered section arranged apically adjacent to the first section, the second section being provided with an anti-rotational means including at least one protrusion extending radially with respect to the axis of the abutment and adapted to cooperate with the dental implant so as to provide rotational guidance to the abutment upon insertion thereof into the implant, and
   the dental implant being provided with a complementary guiding and lock means comprising:
   a first conically tapered section; and
   a second section being provided with an annular platform extending radially with respect to the axis of the dental implant and interposed between grooves, said annular platform being adapted to cooperate with the abutment so as to provide rotational guidance to the abutment upon insertion thereof into the implant,
   wherein the dental implant further comprises a threaded section arranged apically to the second section and the abutment is adapted to axially hold the threaded screw for fastening the abutment to the dental implant,
   wherein the overall axial length of the first and second sections of the abutment, the length of the threaded screw and the position of the threaded screw within the abutment are selected such that threaded engagement of the threaded screw to the dental implant is not possible when the at least one protrusion is held in an intermediate position on the annular platform of the implant, wherein the intermediate position is a position where the longitudinal axes of the guiding and lock means of the abutment and of the implant are coaxial with one another.

2. The system according to claim 1, wherein the guiding and lock means of the abutment further includes a third substantially circular cylindrical section arranged apically adjacent to the second section, so as to provide axial guidance to the abutment upon the insertion thereof into a dental implant, wherein the overall axial lengths of the first, second and third sections of the abutment, the length of the threaded screw and the position of the threaded screw within the abutment are selected such that fastening of the threaded screw to the dental implant is not possible when the at least one protrusion is retained in the intermediate position on the annular platform of the implant.

3. The system according to claim 1, wherein the taper of the first section of the abutment with respect to the axis of the abutment is in the order of about 6° to about 10°.

4. The system according to claim 3, wherein the taper of the first section of the abutment with respect to the axis of the abutment is in the order of about 720 to about 9°.

5. The system according to claim 4, wherein the taper of the first section of the abutment with respect to the axis of the abutment is about 8°.

6. The dental implant system according to claim 1, wherein the annular platform is surrounded by four grooves.

7. The system according to claim 1, wherein the second section of the abutment comprises four straight sides connected by four interposed protruding sides.

8. The system according to claim 1, wherein the overall axial length of the first and second sections of the abutment, the length of the threaded screw and the position of the screw within the abutment are selected such that threaded engagement between the threaded screw and the threaded section of the dental implant is not possible when the at least one protrusion is held in the intermediate position on the annular platform of the implant.

* * * * *

UNITED STATES PATENT AND TRADEMARK OFFICE
CERTIFICATE OF CORRECTION

PATENT NO.        : 8,408,904 B2
APPLICATION NO.   : 11/921480
DATED             : April 2, 2013
INVENTOR(S)       : Johnny Purga et al.

It is certified that error appears in the above-identified patent and that said Letters Patent is hereby corrected as shown below:

In the Claims

It Should Read:

Column 9, Lines 4-6 (Claim 4, line 3): The system according to claim 3, wherein the taper of the first section of the abutment with respect to the axis of the abutment is in the order of about 7° to about 9°.

Signed and Sealed this
Twenty-first Day of April, 2015

Michelle K. Lee
*Director of the United States Patent and Trademark Office*